(12) United States Patent
Deshpande

(10) Patent No.: US 6,830,375 B2
(45) Date of Patent: Dec. 14, 2004

(54) ANTI-COLLISION METHOD AND APPARATUS FOR USE WITH C-ARM X-RAY MACHINE

(75) Inventor: Piyush Vijay Deshpande, Nagpur (IN)

(73) Assignee: GE Medical Systems Global Technology Company, Inc., Waukesha, WI (US)

( * ) Notice: Subject to any disclaimer, the term of this patent is extended or adjusted under 35 U.S.C. 154(b) by 93 days.

(21) Appl. No.: 10/233,834

(22) Filed: Aug. 30, 2002

(65) Prior Publication Data

US 2004/0042587 A1 Mar. 4, 2004

(51) Int. Cl.⁷ ................................................ H05G 1/02
(52) U.S. Cl. ...................................... 378/197; 378/198
(58) Field of Search ................................. 378/195–198

(56) References Cited

U.S. PATENT DOCUMENTS

| | | |
|---|---|---|
| 5,570,770 A | 11/1996 | Baaten et al. |
| 6,430,259 B2 * | 8/2002 | Meek et al. ................ 378/117 |
| 6,609,826 B1 * | 8/2003 | Fujii et al. ................... 378/198 |
| 2001/0022831 A1 | 9/2001 | Meek et al. |

FOREIGN PATENT DOCUMENTS

| | | |
|---|---|---|
| DE | 693 27436 T2 | 2/2000 |
| DE | 2120344 A | 3/2003 |
| EP | 0 588 418 B1 | 3/1994 |
| JP | 6-278082 | 10/1994 |
| JP | 9-238931 | 9/1997 |
| JP | 517866 A | 3/2003 |
| WO | WO 01/45562 A2 | 12/1971 |

* cited by examiner

*Primary Examiner*—Craig E. Church
(74) *Attorney, Agent, or Firm*—Joseph S. Heino; Patrick M. Bergin; Q. Todd Dickinson

(57) ABSTRACT

An anti-collision method and apparatus for use with a C-arm x-ray imaging machine to prevent damage to the imaging apparatus and injury to patients and health care workers includes a load cell, a differential buffer and integrator, an analog to digital converter, and a microcontroller controlling the motor drive. The present invention also provides a method for controlling the apparatus via a microcontroller and includes the steps of determining whether an up/down switch is actuated, reading and comparing a value with a tabulated value, halting the C-arm if the difference between the tabulated value and the recorded value exceeds a threshold value and reversing the apparatus.

22 Claims, 4 Drawing Sheets

LOAD CURVE WITHOUT EXTERNAL FORCE

| SR. NO | HEIGHT cm | UP kg | DOWN kg |
|---|---|---|---|
| 1 | 0 | 52 | 49.7 |
| 2 | 10 | 58.8 | 49.4 |
| 3 | 20 | 60.3 | 48.7 |
| 4 | 30 | 62.5 | 46.7 |
| 5 | 40 | 64.8 | 44 |
| 6 | 45 | 68.2 | 41.6 |

…

ANTI-COLLISION METHOD AND APPARATUS FOR USE WITH C-ARM X-RAY MACHINE

BACKGROUND OF THE INVENTION

1. Field of the Invention

The present invention relates generally to the field of x-ray imaging systems. More specifically, it relates to an anti-collision method and apparatus for use with a C-arm x-ray imaging machine for preventing serious collisions between patients, operators and the equipment itself.

2. Background of the Invention

It is frequently desired to conduct an x-ray examination of a patient from several different positions and is often preferable to do so without the need to reposition the patient. Mobile C-arm X-ray diagnostic machines, such as that shown in FIG. 1, have been developed to meet these needs and are now well known in the medical and surgical arts. The C-arm x-ray machine is especially useful in that it is small enough and mobile enough to be present in an operating or exam situation without requiring the physician to repeatedly move or requiring the patient to change positions to obtain a suitable image.

The term "C-arm" refers to the C-shaped member of the machine that contains an x-ray source and an image receptor mounted on opposing ends of the C-arm such that x-rays emitted by the source are incident on and detected by the image receptor. The source and the image receptor are positioned such that when, for example, a human extremity is interposed between the x-ray source and the image receptor and irradiated with x-rays, the receptor produces data representative of characteristics of the interposed object. The data produced is typically displayed on a monitor and electronically stored.

The C-arm itself is normally mounted such that it is permitted two degrees of freedom. First, the C-arm track is slidably mounted to the support member so as to be movable in relation to the support member. This permits the x-ray source and image receptor to be moved rotatably about the arc of curvature of the track in the C-arm. The C-arm support member also permits rotation of the C-arm about its axis. Often the support member is in the general shape of an L and is referred to as the L-arm, or yoke. Mobile C-arms have a third degree of freedom in that they are free to move horizontally along the floor and a fourth degree of freedom because the C-arm can be moved both upwardly and downwardly.

Obviously, a support structure that permits rotation and movement of such a C-arm must be constructed to withstand large torsional, tensile and compressive stresses. It is also desirable to provide a support structure heavy enough and a center of gravity low enough to avoid tipping when the C-arm is raised and rotated, which in some cases causes a dramatic shift in the center of mass of the equipment.

Additionally, C-arm x-ray equipment must be delicately positioned in order to render the image or images desired by the physician. Unfortunately, the weight of the support structure makes it difficult to position the C-arm. Therefore, it is desirable to design a source of frictional drag between the C-arm and the support member as well as on the C-arm track. It is also desired to provide an electric motor to move the C-arm both up and down due to the weight of the apparatus.

The delicate nature of the x-ray equipment requires delicate handling. Additionally, patients needing x-rays often require careful handling. In order to make the C-arm x-ray safer for the patient and to reduce the likelihood of damage to the C-arm itself, the device of the present invention provides for an anti-collision alarm and mechanism that stops movement of the C-arm upon contact with an object and then reverses movement of the C-arm to release the force exerted on the object by the machine.

SUMMARY OF THE INVENTION

It is therefore an object of the present invention to provide a method and an apparatus for use with a C-arm x-ray machine that emits a warning when the C-arm has run into an object, such as a patient, a gurney, or other obstacle. It is yet another object of the present invention to provide for such a method and apparatus that stops the C-arm when a part of it runs into an obstacle such that no damage occurs to the obstacle or to the C-arm, and prevents injury to the patient. A further object of the present invention is to provide such a method and apparatus that includes a programmable device in which the threshold of force required to stop the C-arm and sound the alarm may be varied. It is yet another object of the present invention to provide such a method and apparatus that requires relatively few parts, that can be easily manufactured and that can be readily installed on new or existing equipment.

The device of the present invention has obtained these objects. It provides for a load cell that is mounted at the bottom of the vertical column of the C-arm x-ray machine. This load cell converts the load, or the dynamic change in the load, on the vertical column into an electrical signal. The electronic signal is directed to an electronic circuit that filters and buffers the signal. The filtered signal is directed to a microcontroller. The microcontroller compares the load value with a database of preset load values and can operate to turn off the electric motor that raises and lowers the C-arm if the difference between the force on the load cell and the force expected by the microcontroller is greater than a certain amount. The microcontroller is adjustable such that the amount of force required to stop the motor can be varied. The electronic circuit in the method and apparatus of the present invention then reverses the electric motor to release the force exerted by the machine. Additional objects and advantages of the invention will be set forth in the description that follows. Other objects and advantages may be learned by practice of the invention.

BRIEF DESCRIPTION OF THE DRAWINGS

FIG. 3A is a tabular example of a Look Up Table (LUT) and FIG. 3B is a graphic example of an LUT.

DETAILED DESCRIPTION

The following detailed description is intended to describe the preferred embodiments that are depicted in the figures. It is to be understood that changes could be made to that which is specifically described and shown that would still fall within the scope of the present invention.

Figure 1A:
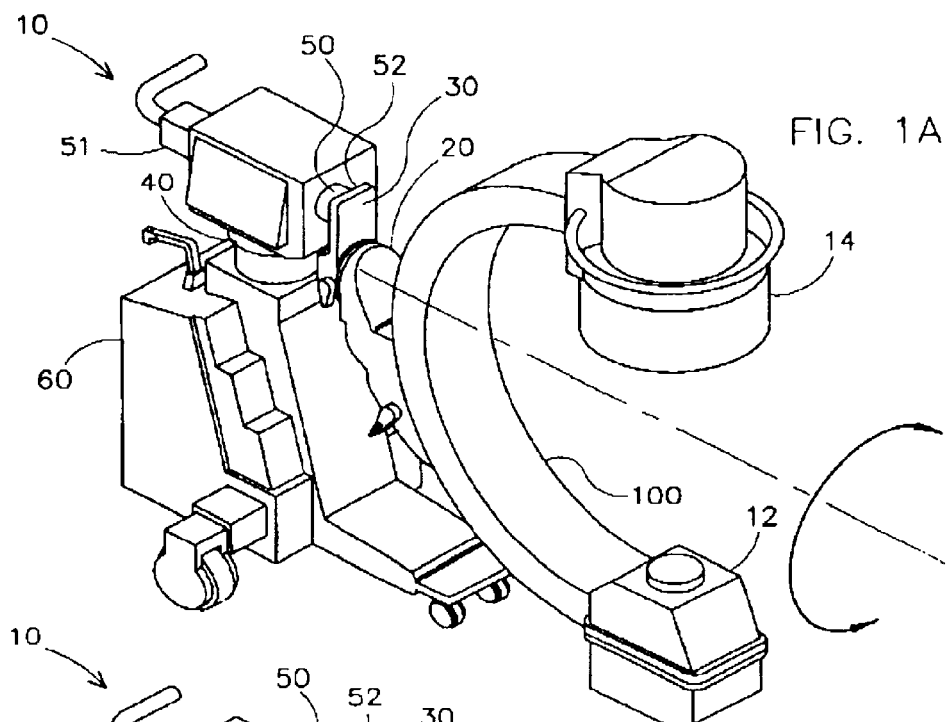
FIGS. 1A and 1B illustrate a C-arm x-ray machine that utilizes the method and apparatus of the present invention.
Figure 1B:
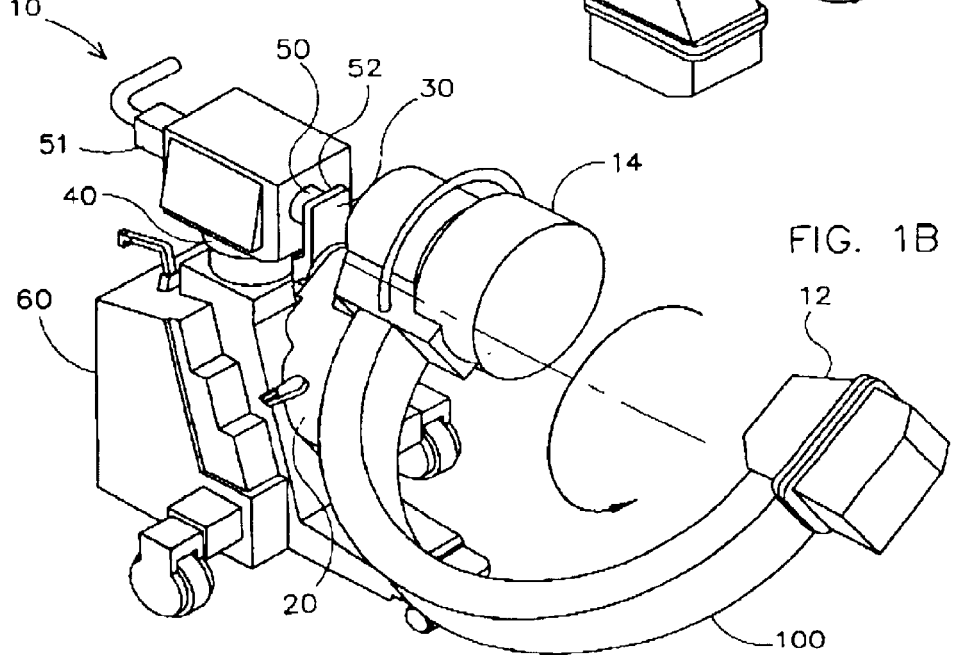

Referring now to the drawings in detail, wherein like numbered elements refer to like elements throughout, FIGS. 1A and 1B depict the basic components of the C-arm x-ray imaging system with which the method and apparatus of the present invention is utilized. In general, the C-arm x-ray imaging machine, generally identified 10, is comprised of the following components: a support base having a vertically extendable column, a C-arm mounting apparatus providing movement of the C-arm in several directions, the C-arm 100, an x-ray source 12, an image receptor 14, an image processing system, a display and viewing system, a high voltage generator and a control unit.

The x-ray source 12 preferably comprises an x-ray tube and a high-voltage generator. The high-voltage generator is preferably connected to an adjustable high-voltage power supply capable of generating approximately −70 kV to −120 kV. The x-ray source 12 is generally a scanning beam x-ray in which charged particles are scanned across a target assembly. The x-ray source 12 generally includes a series of deflection coils under the control of a scan generator. High-energy charged particles are generated within a vacuum chamber and then scanned across the target. When the system is operated, the charged particle beam strikes the target and generates x-ray photons. The x-ray photons preferably pass through a collimator and form an x-ray beam. The x-ray beam has an axis that is substantially aligned with the center of the active area of the x-ray detector. The x-ray beam has a vector that is defined by the axis of the x-ray beam in the direction of the x-ray detector assembly. The imaging object generally refers to the patient. X-rays that have passed through the patient are detected and later processed for some form of interpretation.

The image receptor 14 captures the x-ray photons scanned across the imaging object and converts them to electrical signals. The impulses are then converted to digital data and either stored or directed immediately into a computer for image reconstruction. The imaging process system generally consists of a computer with a software package that reconstructs the image and displays the image on a screen and a device that provides for storage of the image. The display system and the control unit are normally remotely operated. Thus the operator can be shielded from radiation but still perform the x-ray. Alternatively, the entire system can be placed in an examining or operating room so that the health care provider can view images of the patient in real time.

The mobile C-arm x-ray imaging machine, generally identified 10, is comprised of a wheeled support base 60. In a preferred embodiment the support base 60 is a generally rectangular upright body that may be equipped with one or more video monitors and has an upper portion or vertically extendable column 40 with an extendable cross arm 50. The support base 60 generally features a vertical column 40 used to raise and lower the cross arm 50. The vertical column 40 raises and lowers the cross arm 50, which in turn raises and lowers the C-arm apparatus, which is generally comprised of the support arm 30, the yoke, 20 and the C-arm 100. The vertical column 40 is generally between the support base 60 and the vertically extendable column 40 and bears the entire weight of the C-arm 100. The vertical column 40 is generally both raised and lowered using an electric motor (not shown). The extendable cross arm 50 has a first portion 51 slidably mounted within the vertically extendable column 40 and a second end 52 having an aperture in the end of the cross arm 50. The support base 60 is important to the imaging system 1 in that it provides a platform for the yoke 20 and the C-arm 100. Therefore, the support base 60 should have a footprint large enough such that the yoke 20 and C-arm 100 are permitted to rotate and can be lifted and lowered without the danger of tipping and/or the support base 60 must be heavy enough to prevent tipping of the C-arm x-ray machine 10.

Figure 2:
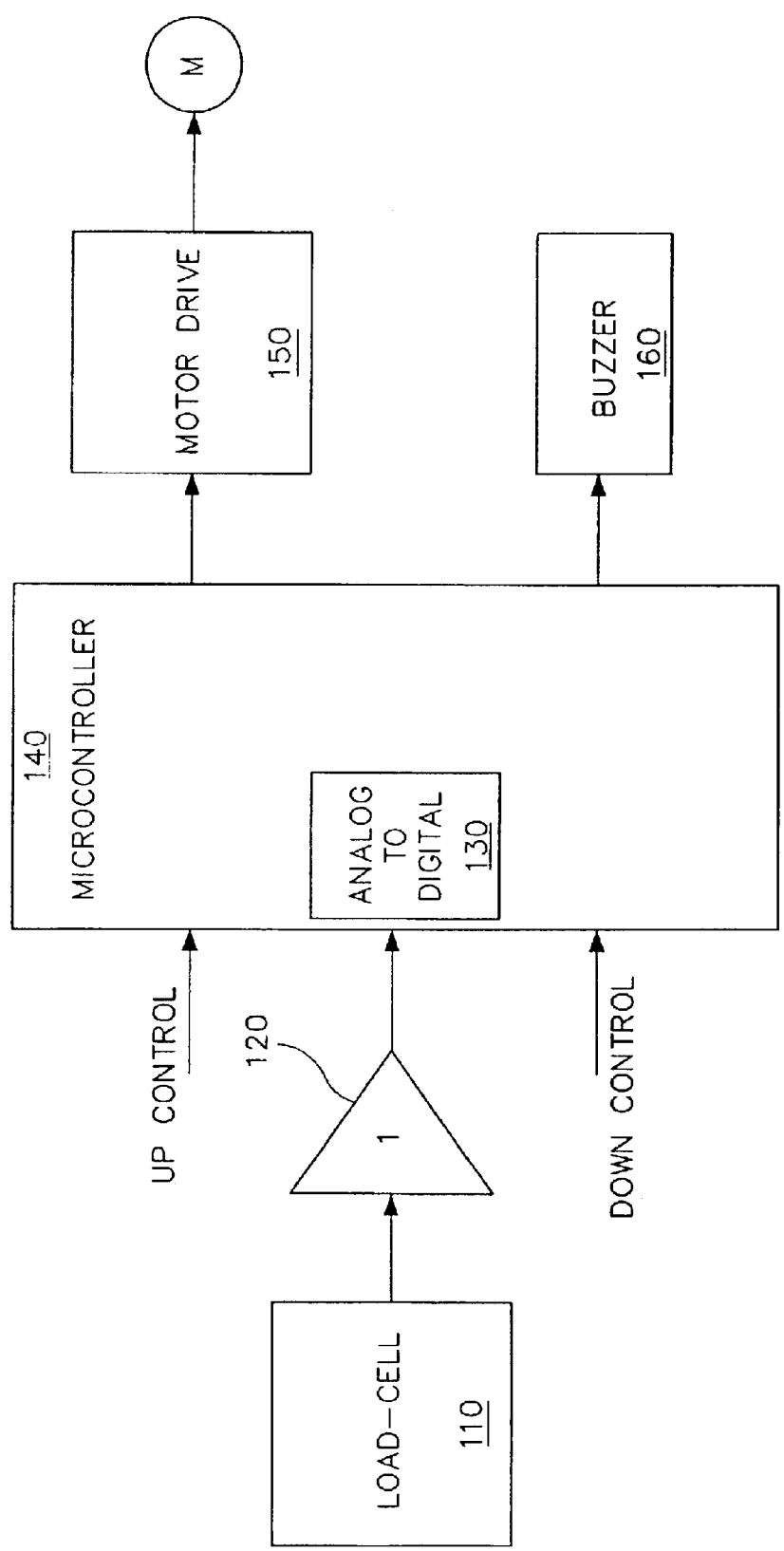
FIG. 2 is a flow chart summarizing the workflow of the present invention.
Figure 4:
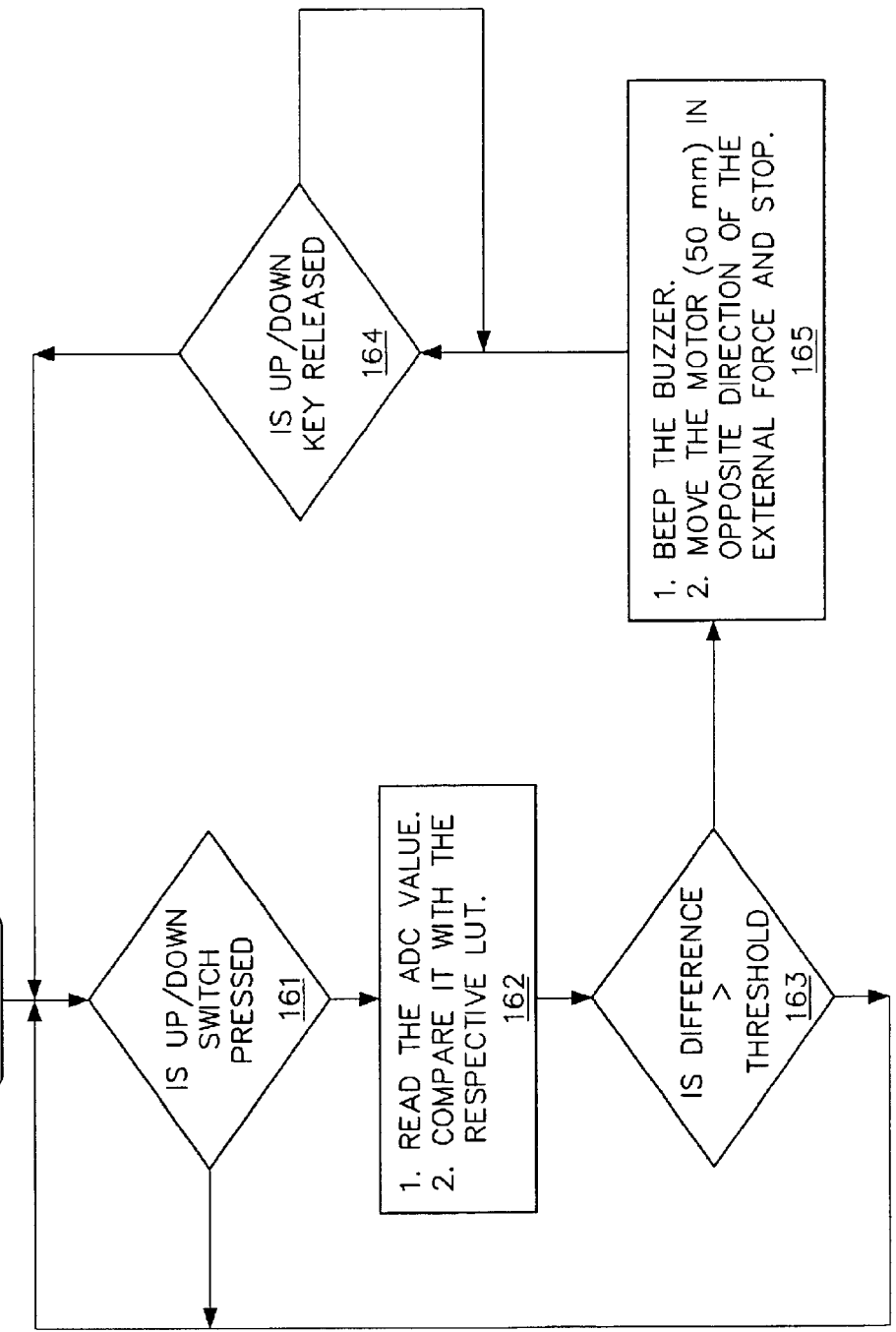
FIG. 4 is a flow chart also summarizing the workflow of the present invention.

FIGS. 2 and 4 are schematic summaries of the workflow of the method and apparatus of the present invention. From rest, the C-arm 100 is activated to move the vertical column 40 either up or down 161. A microcontroller 140 is provided and the microcontroller 140 reads the analog to digital converter 130 and compares it with the value in a Look Up Table 162 (or "LUT"). The microcontroller 140 then determines whether the difference between the value reported and the value in the LUT is greater than the allowable, or threshold, value 163. If it is not, the process continues the up or down movement 161. If the threshold 163 is met or exceeded, the C-arm 100 is halted 164, an audio alarm, or buzzer, is sounded 165 and the motor M is reversed 165 incrementally and then stopped 165.

As shown in FIG. 2, the method and device of the present invention provide for a load cell 110 mounted at some point along the bottom of the vertical column 40. The load cell 110 is capable of sensing the proportional change of the resistivity of the material of the vertical column 40 and emits an electronic signal proportional to that change.

The electronic signal is directed from the load cell 110 to a differential buffer and an integrator 120 to isolate and filter the signal. The filtered signal is then routed to an analog to digital converter 130. The analog to digital converter 130 is often part of a microcontroller 140, as shown in FIG. 2.

Figures 3A, 3B:
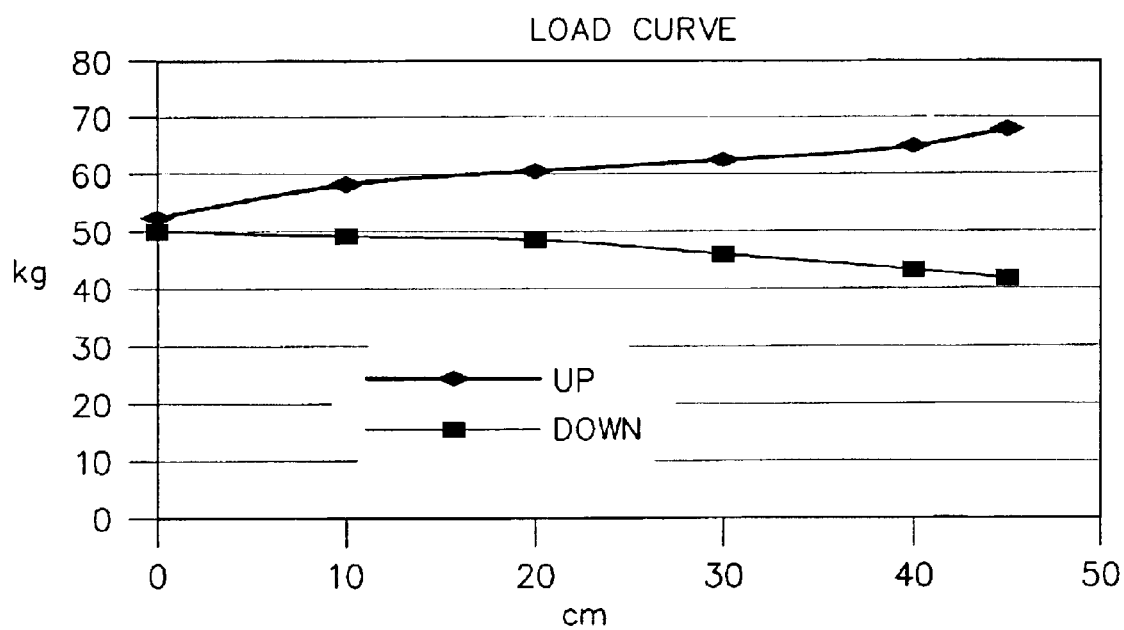
FIGS. 3A and 3B are diagrams illustrating load curves that may be employed in accordance with the method and apparatus of the present invention. More specifically.

The microcontroller 140 effectively reads the output from the analog to digital converter 130 and compares it with reference values in an LUT, such as the one shown in FIG. 3A. If the difference between the output of the load cell 110 is larger than the reference value in the LUT, the microcontroller 140 sends a signal to the motor drive 150 that stops the motor drive 150 and sends a signal to a buzzer 160, which alerts the operator to the potential problem. It is often advantageous to program the microcontroller 140 to operate the motor drive 150 in the reverse direction to alleviate the force on the obstacle as well as the force on the C-arm 100.

The LUTs are created by operating the C-arm 100 over its full range of motion in the absence of obstacles and recording the values at different heights. It is preferred to have four sets of LUTs, one for upward motion of the C-arm 100, one for downward motion of the C-arm 100. The other two LUTs are designed to be used when the C-arm 100 is activated for initial movement of the C-arm 100 in both the upward and downward directions. The weight and weight distribution of the C-arm 100 combine to create a spike in the load recorded by the load cell 110 during the initial movement of the C-arm 100. During an initial jerk, the input value is compared with an LUT specifically designed for either upward or downward jerks. Obviously, this spike is not related to an encounter with an obstacle and the inventors do not wish for the C-arm 100 to reverse itself at that point of operation.

An LUT is nothing more than an index of the position of the vertical column 40 as measured by a multi-turn potentiometer and a gear assembly versus the amount of force recorded by the load cell 110 converted to digital. A baseline value is first established for each position along the vertical column 40. Baseline values are then established by starting movement of the C-arm 100 in both upward and downward directions at each point along the vertical column's 40 range of motion. The amount of force required before the motor drive 150 is reversed can be varied, depending on the desired sensitivity of the system.

FIGS. 3A and 3B are simple examples of LUTs. Each table describes the load on the load cell 110 in the absence of external force over the range of vertical motion of the column 40. As can be observed from the figures, the load varies over the range of the vertically extendable column 40. Two more sets of LUTs are necessary in the preferred embodiment. Those LUTs would account for the larger forces encountered when the C-arm 100 is initially moved.

It is to be understood that the invention is not limited to the embodiments set forth herein but that the invention may be carried out in other ways without departure from the spirit of this invention.

What is claimed is:

1. An X-ray imaging apparatus having
  a mobile support base,
  an extendable and retractable vertical column attached to the support base, said vertical column is powered by an electric motor,
  an extendable cross arm having a first end slidably attached to the vertical column and a second end,
  a yoke having a first end attached to the second end of the cross arm,
  a C-arm attached to the yoke,
  an x-ray source,
  an image receptor,
  wherein the image receptor and the x-ray source are mounted on opposing ends of the C-arm, and
  an anti-collision device that comprises means for detecting an increase in force exerted on the vertical column and stopping the movement of said vertical column.

2. The anti-collision device of claim 1 wherein the vertical column force detecting means comprises
  a load cell is mounted on the vertical column emits an electronic signal proportional to the force on the vertical column,
  an analog to digital controller converts the data from the load cell from analog to digital,
  a plurality of predetermined force values according to certain Look Up Tables (LUTs) are stored in the memory of a microcontroller,
  wherein, if the force detected by the load cell exceeds the predetermined force value in the LUT, the microcontroller sends an electronic signal to the electric motor to stop the motor.

3. The anti-collision device of claim 2 wherein the microcontroller sends an electronic signal to a speaker and the speaker emits a warning noise when the force detected by the load cell exceeds the predetermined force value in the LUT.

4. The anti-collision device of claim 3 wherein at least four LUTs are utilized, said LUTs including, but not limited to,
  an LUT providing force values as the C-arm is moved upwardly,
  an LUT providing force values as the C-arm moves down,
  an LUT providing initial force values throughout the upward range of motion of the C-arm, and
  an LUT providing initial force values throughout the downward range of motion of the C-arm.

5. The anti-collision device of claim 4 wherein the microcontroller is programmed to first stop the electric motor if the force detected by the load cell exceeds the predetermined force value in the LUT and then to reverse the direction of the C-arm movement.

6. An X-ray imaging apparatus comprising
  a mobile support base,
  an electric motor installed within the support base,
  a gear assembly driven by the electric motor,
  a vertical column driven by the gear assembly, said vertical column including means for detecting an increase in force on the column and stopping the progress of movement of the vertical column,
  an extendable cross arm having a first end slidably attached to the vertical column and a second end,
  a yoke having a first end attached to the second end of the cross arm,
  a C-arm attached to the yoke,
  an x-ray source, and
  an image receptor,
  wherein the image receptor and the x-ray source are mounted on opposing ends of the C-arm.

7. The X-ray imaging apparatus of claim 6 wherein the vertical column includes means for detecting an increase in force exerted on the column and stopping movement at the vertical column.

8. The X-ray imaging apparatus of claim 6 wherein
  a load cell is provided that is mounted on the vertical column and emits an electronic signal proportional to the force on the vertical column,
  an analog to digital controller converts the data from the load cell from analog to digital,
  a plurality of predetermined force values in accordance with a number of Look Up Tables (LUTs) are stored in the memory of a microcontroller,
  wherein if the force detected by the load cell exceeds the predetermined force value in the LUT the microcontroller sends an electronic signal to the electric motor to stop the motor.

9. The X-ray imaging apparatus of claim 8 wherein the microcontroller sends the electronic signal to a speaker and the speaker emits a warning noise when the force detected by the load cell exceeds the predetermined force value in the LUT.

10. The X-ray imaging apparatus of claim 9 wherein at least four LUTs are employed, said LUTs including, but not limited to,
  an LUT providing force values as the C-arm is moved upwardly,
  an LUT providing force values as the C-arm moves down,
  an LUT providing initial force values throughout the upward range of motion of the C-arm, and
  an LUT providing initial force values throughout the downward range of motion of the C-arm.

11. The X-ray imaging apparatus of claim 10 wherein the microcontroller is programmed to first stop the electric motor if the force detected by the load cell exceeds the predetermined force value in the LUT and then to reverse the direction of the C-arm.

12. An X-ray imaging apparatus comprising
  a mobile support base,
  an electric motor installed within the support base,
  a gear assembly driven by the electric motor,
  a vertical column driven by the gear assembly,
  a load sensor mounted on the vertical column,
  a microcontroller electronically connected to the load sensor, and to the electric motor,
  wherein, if the load sensor detects a load in excess of that programmed into the microcontroller, the microcomputer sends a signal to the electric motor to stop, an extendable cross arm having a first end slidably attached to the vertical column and a second end, a yoke having a first end attached to the second end of the cross arm, a C-arm attached to the yoke, an x-ray source, an image receptor, wherein the image receptor and the x-ray source are mounted on opposing ends of the C-arm.

13. The X-ray imaging apparatus of claim 12 wherein the microcontroller sends an electronic signal to a speaker and the speaker emits a warning noise when the force detected by the load cell exceeds the predetermined force value in the LUT.

14. The X-ray imaging apparatus of claim 13 wherein at least four LUTs are used, said LUTs including, but not limited to, an LUT providing force values as the C-arm, is moved upwardly, an LUT providing force values as the C-arm moves down, an LUT providing initial force values throughout the upward range of motion of the C-arm, and an LUT providing initial force values throughout the downward range of motion of the C-arm.

15. The X-ray imaging apparatus of claim 14 wherein the microcontroller is programmed to first stop the electric motor if the force detected by the load cell exceeds the predetermined force value in the LUT and then to reverse the direction of the C-arm.

16. An X-ray imaging apparatus comprising a mobile support base, an electric motor installed within the support base, a gear assembly driven by the electric motor, a multi-turn potentiometer, a vertical column driven by the gear assembly wherein the vertical motion is controlled by cooperation of the potentiometer and the gear assembly, a load sensor mounted on the vertical column, a microcontroller electronically connected to the load sensor, and to the electric motor, wherein when the electric motor drives the vertical column and if the load sensor detects a load in excess of that programmed into the microcontroller while the C-arm is moving the microcontroller sends a signal to the electric motor to stop, a C-arm X-ray imaging apparatus.

17. The X-ray imaging apparatus of claim 16 wherein the microcontroller is programmed to send a signal to the electric motor to reverse.

18. The X-ray imaging apparatus of claim 17 wherein the microcontroller compares the force value received from the load sensor with the baseline value in four LUTs, an LUT providing tone values as the C-arm is moved upwardly, an LUT providing force values as the C-arm moves down, an LUT providing initial force values throughout the upward range of motion of the C-arm, an LUT providing initial force values throughout the downward range of motion of the C-arm, and wherein if the value of the force recorded by the load sensor exceeds the value of the force recorded in the LUT for that particular position, the C-arm, the microcontroller sends an electronic signal to stop the electric motor.

19. For use in a C-arm x-ray machine having a moveable vertical column for moving the C-arm, vertically, a method for detecting an increase in load on the vertical column of the C-arm X-ray machine comprising the steps of determining whether the C-arm is being moved upwardly or downwardly along the vertical column, detecting a change in load on the vertical column, sending a signal to a microcontroller reflecting the change in load, comparing the signal with a table of previously recorded signals reflecting average values, determining whether the new value is greater than the previously recorded value, stopping movement of the C-arm if the value exceeds the recorded value, and continuing movement of the C-arm if the value does not exceed the reference value.

20. The method of claim 19 wherein there are four sets of previously recorded values called Look Up Tables (LUTs) including an LUT with recorded values for upward movement, an LUT with recorded values for downward movement, an LUT with recorded values for initial upward movement, and an LUT with recorded values for initial downward movement.

21. The method of claim 20 wherein the microcontroller is programmed to reverse the direction of the C-arm if, after it stops the C-arm, the load exceeds a specified threshold.

22. The method of claim 21 including, prior to said C-arm stopping step, the steps of providing an audio alarm and actuating the audio alarm.

* * * * *